United States Patent
Nozaki et al.

(10) Patent No.: US 6,214,774 B1
(45) Date of Patent: Apr. 10, 2001

(54) GREASE FOR FAN BEARING

(75) Inventors: Seiichi Nozaki, Okayama-ken; Takahiro Koremoto, Iwata; Kazuhiro Matsumoto, Yamato; Yosiki Yamaguchi, Tokyo-to, all of (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 09/398,013

(22) Filed: Sep. 17, 1999

Related U.S. Application Data

(62) Division of application No. 09/010,540, filed on Jan. 22, 1998, now abandoned.

(30) Foreign Application Priority Data

Jan. 27, 1997 (JP) ........................................ 9-12641

(51) Int. Cl.$^7$ .............................................. C10M 115/08
(52) U.S. Cl. ......................... 508/209; 508/211; 508/552; 384/397; 384/429
(58) Field of Search .................... 508/209, 211, 508/552; 384/397, 429

(56) References Cited

U.S. PATENT DOCUMENTS

| | | | |
|---|---|---|---|
| 4,537,691 | * | 8/1985 | Mori et al. ............................. 508/209 |
| 4,759,859 | * | 7/1988 | Waynick et al. ...................... 508/189 |
| 5,084,193 | * | 1/1992 | Waynick et al. ...................... 508/528 |
| 5,192,458 | * | 3/1993 | Minemura et al. ................... 508/209 |
| 5,301,923 | * | 4/1994 | Asad et al. . |

FOREIGN PATENT DOCUMENTS

| | | | |
|---|---|---|---|
| 14 5872 | * | 1/1981 | (DE) . |
| 04253796 | * | 1/1991 | (JP) . |
| 03031394 | * | 2/1991 | (JP) . |
| 11241084 | * | 9/1999 | (JP) . |

* cited by examiner

*Primary Examiner*—Margaret Medley
(74) *Attorney, Agent, or Firm*—Arent Fox Kintner Plotkin & Kahn, PLLC

(57) ABSTRACT

A grease for a bearing of a fan comprises a base oil selected from a various kinds of silicone oils having a viscosity of 30 to 500 mm$^2$/s at 40 degree-C. and a viscosity of 30,000 mm$^2$/s or less at −30 degree-C., and a diurea compound, as a thickening agent, at the compounding ratio of 2 to 30%-wt. The urea compound has a general formula of:

$$R_1—NHCONH—R_2—NHCONH—R_3$$

wherein $R_2$ indicates a tolylene group, a diphenylmethan group or a dimethylbiphenylene group, and $R_1$ and $R_3$ respectively indicate a straight chain saturated alkyl group having the number of carbon atoms of 6 to 18, and an alicyclic group, and wherein the ratio of the straight chain saturated alkyl group to the alicyclic group is within a range of 5 to 95 mol-% to 95 to 5%-mol. The grease maintains its properties suitable for use in a fan, and effectively restrict or prevent generation of hoot sound, while providing satisfactory durability and cost-effctiveness.

8 Claims, 3 Drawing Sheets

Fig. 1

| test item and condition | Embodiment 1 | Embodiment 2 | Embodiment 3 |
|---|---|---|---|
| grease constituents: | | | |
|   stearyl amine | 2.5 % | 4.3 % | 4.3 % |
|   cyclohexyl amine | 7.0 % | 4.7 % | 4.7 % |
|   diphenylmethane diisocyanate | 6.5 % | 8.0 % | 8.0 % |
|   dimethyl silicone | 83.5 % | 82.5 % | --- |
|   methylphenyl silicone | --- | --- | 82.5 % |
|   antioxidant | 0.5 % | 0.5 % | 0.5 % |
| base oil viscosity($mm^2$/s): | | | |
|   (40 °C) | 35 | 70 | 70 |
|   (-30 °C) | 200 | 400 | 500 |
| consistency: | | | |
|   UP   (a) | 267 | 278 | 274 |
|   WP | 280 | 285 | 284 |
| Dropping point (°C) (b): | 250 | 250 | 287 |
| low temp. torque(N·cm) (c): | | | |
|   -30 °C starting torque | 6.2 | 5.7 | 7.1 |
|          rotating torque | 3.0 | 3.3 | 4.1 |
|   -40 °C starting torque | 6.4 | 7.3 | 7.6 |
|          rotating torque | 3.5 | 4.7 | 4.8 |
| whistle sound confirmation test (d-1): | no | no | no |
| whistle sound confirmation test (d-2): | no | no | no |
| grease life (hr)  (e): | <6,000 | <6,000 | <6,000 |

Fig. 2

| test item and condition | Comp. EX. 1 | Comp. EX. 2 | Comp. EX. 3 |
|---|---|---|---|
| | \multicolumn{3}{c}{(commercial grease for fan bearing)} | | |
| thickening agent | teflon | diurea | Li-soap |
| base oil viscosity(mm$^2$/s): <br> (40 °C) <br> (−30 °C) | 550 <br> 65,000 | 123 <br> 300,000(−20°C) | 82 <br> 3,500 |
| consistency: <br> UP (a) <br> WP | 294 <br> 275 | --- <br> 283 | 271 <br> 315 |
| dropping point (°C) (b): | 267 | >240 | 226 |
| low temp. torque(N·cm) (c) <br> −30 °C starting torque <br> rotating torque <br> −40 °C starting torque <br> rotating torque | 27.4 <br> 13.7 <br> 107.7 <br> 58.6 | 33.1 <br> 18.6 <br> --- <br> --- | 10.8 <br> 3.3 <br> 15.9 <br> 5.1 |
| whistle sound confirmation test (d-1): | yes | yes | no |
| whistle sound confirmation test (d-2): | yes | no | no |
| grease life (hr) (e): | 1,345 | 5,120 | 1,964 |

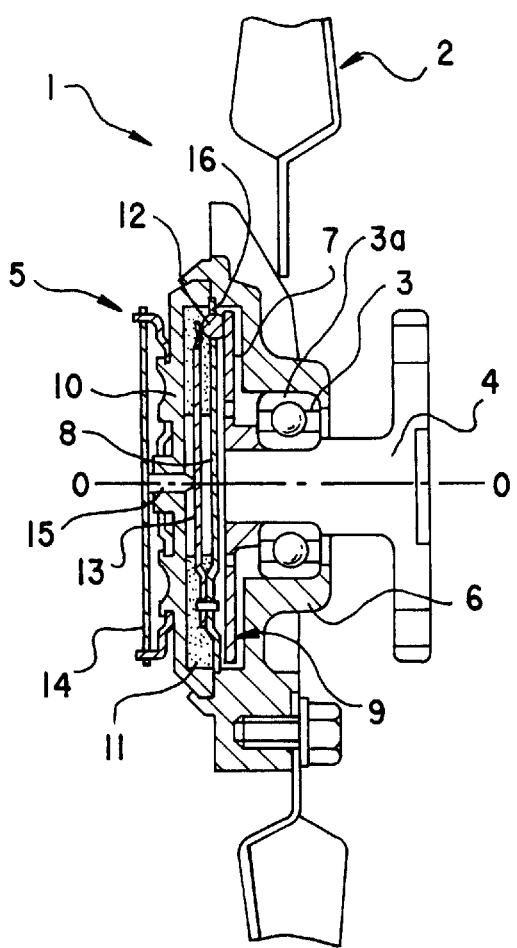
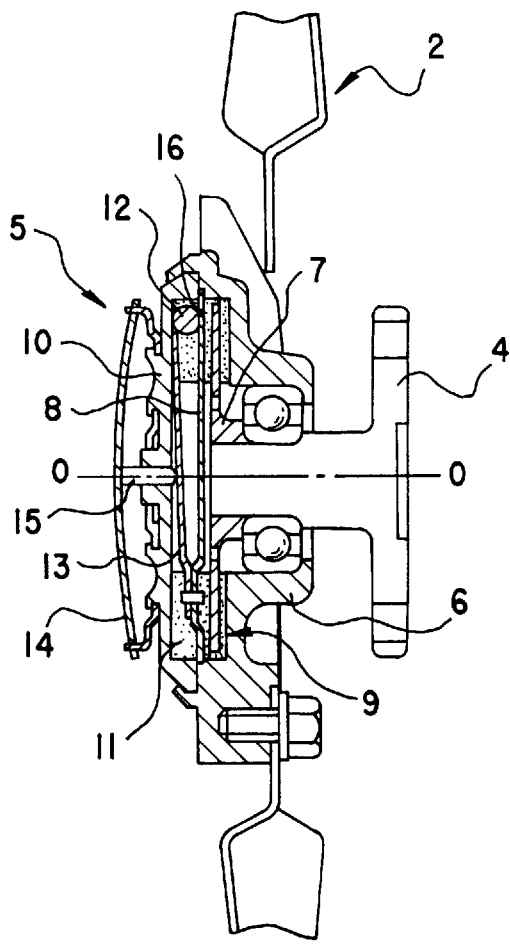
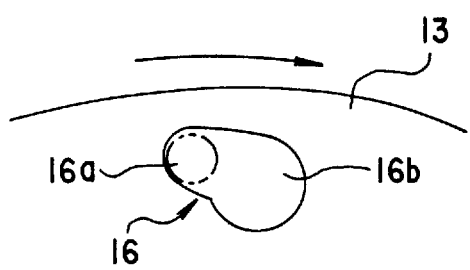

GREASE FOR FAN BEARING

This is a divisional application for U.S. application Ser. No. 09/010,540, filed on Jan. 22, 1998, now abandoned the disclosure of which is hereby incorporated by reference.

BACKGROUND OF THE INVENTION

The invention relates to a grease to be filled in a fan bearing. The term "fan" used in this specification refers to a device for performing a forced cooling relative to cooling water in an engine of an automobile.

It is known that performance and life of a rolling bearing, which is filled with a quantity of grease and sealed for example by a rubber seal, depend on the properties of a grease to be used. A ball bearing for supporting a fan, which performs a forced cooling relative to cooling water in an engine of an automobile, is also filled with a quantity of grease. Thus, it is believed that performance and service life of such a ball bearing are also influenced by the properties of a grease to be used.

Recently, miniaturization and lightening for auxiliary parts of an automobile are facilitated in order to meet a demand for lightening of an automobile. At the same time, such auxiliary parts are also requested to have a high output and a high efficiency. Thus, the reduction in output power of the auxiliary part, due to the miniaturization, is usually compensated for by making its rotational speed higher, it is also noted that the degree of sealing for an engine room is increased, in order to meet the requirement for quieting, so that the temperature within the engine room tends to be increased. Thus, the parts within the engine room are also required to have a durability at higher temperatures.

A fan 1 for an automobile 1 includes, as shown in FIGS. 3(a) and 3(b), an annular casing (rotating member) 6 and a plurality of blades 2 attached to the periphery of the annular casing and extending radially therefrom. The casing 6 is fitted over an outer ring 3a of a ball bearing 3. The fan is rotatably mounted on a main shaft 4 to be driven by an engine. For example, the main shaft 4 is bolted to a flange portion of a pump shaft. A clutch mechanism 5 is disposed between the main shaft 4 and the fan 1. The clutch mechanism 6 is of a temperature sensitive type, so that it is capable of being engaged and disengaged in accordance with variation in the outside air temperature. A torque is transmitted from the main shaft 4 through the clutch mechanism 5 to the fan 1. One example for the construction of the clutch mechanism 5 will be explained below.

A drive disk 7 is securely fitted over the forward end of the main shaft 4 for unitary rotation therewith. A disk-like plate 8 is mounted on the drive disk 7 at its forward end. The plate 8, together with the casing 6, defines a first chamber 9 serving as a torque transmission chamber. A second chamber 11, serving as a reservoir for oil (viscous fluid for the transmission of torque, such as silicone oil), is defined between the plate 8 and a cover 10. A leaf spring 13 is disposed within the second chamber 11. The leaf spring 13 has one end attached to a valve 12 and the other end secured to the plate 8. A bimetal 14 is secured to the cover 10. The bimetal 14 is fitted with a piston 15 which is in alignment with the axis of the main shaft 4.

With the above-mentioned construction, the bimetal 14 is not significantly curved as shown in FIG. 3(a), when the outside air temperature is low. Thus, the piston 15 is forced to urge the leaf spring in the right-hand direction in the drawing. At this time, the valve 12 attached to the leaf spring extends through an aperture 16 formed in the peripheral portion of the plate 8 and is urged against the forward surface of the drive disk 7 within the first chamber 9. The aperture 16 includes, as shown in FIG. 4, an insertion hole 16a and a communication hole 16 in continuation with the insertion hole 16a. The valve 12 is fitted within the insertion hole 16a. A relative velocity is always present between the drive disk 7 and the casing 6, i.e., valve 12. Accordingly, the oil (shown by dots) between the drive disk 7 and the plate 8 is driven, by means of a scraping action of the valve 12 serving as a weir, to be flown through the communication hole 16b into the second chamber 11. Under this condition, substantially the whole quantity of the oil in the first chamber 9 is flown into the second chamber 11, thus only a small quantity of oil remaining in the first chamber 9. Accordingly, the amount of torque transmission is reduced and the rotational speed of the fan 1 is decreased. It is noted that the arrow mark in FIG. 4 indicates the direction in which the drive disk 7 is rotated.

The bimetal 14 is curved as shown in FIG. 3(b), when the outside air temperature is high. Thus, the valve 12 is moved in the left-hand direction of the drawing, so that the piston 15 becomes escaped from the aperture 16 by reason of the resiliency of the leaf spring 13. Accordingly, the above-mentioned scraping action becomes ineffective. By this, the surfaces of the oils within the first and second chambers 9, 11 become to be at the same level, by reason of the communication through the aperture 16. At this time, the effective transmission surface of the first chamber 9 is filled with oil, so that a predetermined torque is transmitted and the rotational speed of the fan 1 is increased.

In the above-mentioned fan, the grease within the ball bearing 3 is required to have an extended life in terms of bearing lubrication at higher temperatures, a low leakage property, and a superior performance at low temperatures.

In order to meet the above-mentioned requirements, greases have been conventionally used which are formed by combining a urea based thickening agent with a synthetic oil as a base oil, by combining a fluoro thickening agent with a fluoro silicone oil or a fluoro oil as a base oil, or by combining a Li-soap thickening agent with a silicone oil as a base oil.

When the above-mentioned fan is operated under cold environment (in winter), an unusual sound (a hoot sound) may be generated, depending upon the specification of the fan or operation conditions. It is noted, however, that the hoot sound under cold environment is not always generated. It is also noted that the hoot sound is generated only a short time. Specifically, the hoot sound is generated upon starting an engine of an automobile and not caused thereafter. Since the hoot sound has such complex characteristics, the reason why it is caused has not yet been clarified. It is also noted that the fan used in an automobile is operated at high temperatures and high speeds, and its durability is one of the important characteristics. No effective measures for preventing generation of hoot sound, however, have been provided heretofore.

It has been studied in prior art to employ, as a countermeasure for preventing generation of hoot sound, a low viscosity grease which has a superior characteristics at lower temperatures (for example, forming an even oil film between the balls and the raceway surfaces of the inner and outer rings under cold environment, and having satisfactory flowability). The countermeasure is intended to restrict generation of the hoot sound by increasing the lubricity of the grease under cold environment. It is noted, however that such a grease has a low viscosity, so that, when a grease consisting of the combination of a synthetic oil (base oil) and an urea (thickening agent), or the combination of a silicone oil (base oil) and a Li-soap (thickening agent) is employed, it is expected that a satisfactory lubricity at higher temperatures would not be obtained and that durability would be decreased. It is also mentioned that the combination of a fluoro oil (base oil) and a fluoro thickening agent is not cost-effective.

SUMMARY OF THE INVENTION

This invention is to provide a means for effectively restricting or preventing generation of hoot sound, while, at the same time, maintaining the function of a fan, as well as providing satisfactory durability and cost-effectiveness.

In order to achieve the above object, the invention provides a grease which is featured by comprising, as a base oil, a silicone oil having a viscosity from 30 to 500 mm$^2$/s at 40 degree-C. and 30,000 mm$^2$/s or less at −30 degree-C., and, as a thickening agent, a diurea compound at a compounding ratio of 2 to 30%-wt., the diurea compound having the general formula of:

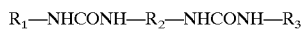

$R_1$—NHCONH—$R_2$—NHCONH—$R_3$ wherein: $R_2$ indicates a tolylene group, a diphenylmethylene group or a dimethylbiphenylene group. $R_1$ and $R_3$ indicate respectively saturated straight chain alkyl groups having the number of carbon atoms from 6 to 18, and alicyclic groups. The ratio between $R_1$ and $R_3$ is within the range of 5 to 95%-mol of the straight chain saturated alkyl groups to 95 to 5%-mol of the alicyclic groups.

That is to say, the grease of the invention is a composition produced by combining a silicone oil, as a base oil, with a special urea compound having compatibility with such silicone oil.

Amines to be used in the above-mentioned reactions may include:

n-propylamine, isopropylamine, n-butylamine, isobutylamine, s-butylamine, n-pentylamine, 3-methylbutylamine, n-heptylamine, n-octylamine, 2-ethylhexylamine, n-tetradecylamine, n-hexadecylamine, n-octadecylamine, n-octadecylamine, aniline, 4-biphenylamine, p-phenetidine, p-anisidine, p-dodecylaniline, cyclopentylamine, cyclohexylarmine, dihydroabiethylamine, 3,5,5-trimethylhexylamine, oleylarnine and the like.

Isocyanates to be used in the above-mentioned reactions may include:

1,5-naphthylenediisocyanate, 4,4'-diphenylmethanediisocyanate, 2,4-tolylenediisocyanate, 3,3'-dimethyl-4,4'biphenylenediisocyanate, hexamethylenediisocyanate and the like.

The compounding ratio of the urea based thickening agent in the grease is preferably in the range of 2 to 30%-wt. This is because, when such a thickening agent in the amount less than 2%-wt is used, a grease in a liquid state having poor viscosity is produced, which tends to cause leakage easily and which is difficult to satisfactorily seal a bearing. It is also noted, however, that, when such a thickening agent in the amount exceeding 30%-wt is used, a grease in a solidified state having a consistency of 200 or less is produced, which has less serviceability for sealing a bearing.

It is noted that, if desired, antioxidants, preservatives, extreme-pressure agents, oiliness agents or the like may be added to the grease, provided that such agent(s) do not give adverse effects on the advantages of the invention.

In order to obtain the above-mentioned grease, a quantity of solution consisting of two kinds of amines dissolved in a base oil is put into a solution consisting of diisocyanate mixed with a base oil, so as to form a mixed solution. The mixed solution is vigorously agitated, so as to facilitate the reaction process. Then, the mixed solution is heated and agitated until it reaches a temperature of 170 degree-C. The mixed solution is maintained at a maximum heating temperature for a predetermined period of time and then the heating operation is stopped. Thereafter, the mixed solution is cooled at a room temperature. When the mixed solution becomes a temperature of approximately 100 degree-C, requisite additives are added to the mixed solution. A desired operation, such as mixing, is performed for dissolution of the additives. The mixed solution is cooled until it reaches a room temperature. Then, a conventional finishing operation by means of a three-staged roll mill is performed, whereby a bearing grease of the invention may be easily obtained.

In accordance with the invention, a various kinds of silicone oils and diurea compounds are used respectively as a base oil and a thickening agent. Thus, the grease according to the invention provides a satisfactory lubricity over a wide range from lower temperatures to higher temperatures. The grease according to the invention also prevents generation of hoot sound under cold environment and maintains a superior durability at higher temperatures over an extended period of time, whereby increasing the service life of a bearing.

BRIEF DESCRIPTION OF THE DRAWING

FIG. 1 is a table showing a test result of the material properties and performance of greases according to the invention.

FIG. 2 is an evaluation result of the material properties and performance of greases according to comparative examples.

FIG. 3 is a cross-sectional view of a fan to which the grease of the invention is to be applied, wherein FIG. 3(a) shows the fan when the outside air temperature is low, and FIG. 3(b) shows the fan when the outside air temperature is high.

FIG. 4 is a front view showing a portion of a plate partly constituting the fan.

DESCRIPTION OF PREFERRED EMBODIMENTS

A grease according to the invention is filled within a ball bearing fitted over the inner diameter of a fan 1 shown in FIG. 3. The grease of the invention is constituted by a base oil selected from a various kinds of silicone oils having a viscosity of 30 to 500 mm$^2$/s at 40 degree-C. and 30,000 mm$^2$/s or less at −30 degree-C., and a thickening agent selected from special diurea compounds, the compounding ratio of the thickening agent relative to the base oil being 2 to 30%-wt.

The urea compounds are represented by a general formula of: $R_1$—NHCONH—$R_2$—NHCONH—$R_3$, wherein $R_2$ represents a tolylene group, diphenylmethylene group or dimethylbiphenylene group, and wherein $R_1$ and $R_3$ respectively represent saturated straight chain alkyl groups having the number of carbon atoms of 6 to 18 and alicyclic groups. The ratio of the saturated straight chain alkyl groups relative to the alicyclic groups ranges from 5 to 95%-mol to 95 to 5%-mol.

The silicone oils constituting the main portion of the invention have superior characteristics at lower temperatures, so that they do not tend to solidify even at ultra low temperatures below −60 degree-C. and maintain their flowability. It is also noted that the silicone oils have a high flush point more than 300 degree-C., as well as very low evaporation loss at higher temperatures. They also have a superior oxidation stability, as well as a high lubricity, at higher temperatures.

Accordingly, the greases according to the invention have a particularly extended service life and a high lubricity over a wide range from lower temperatures to higher temperatures, as compared with conventional greases which have been widely used and formed by using, as a base oil, mineral oils, a various kinds of esters, poly-alpha-olefin oils or the like.

It is believed that generation of hoot sound under cold environment, which is problematic to a fan bearing, is influenced by the properties at a low temperature and viscosity of a base oil contained in a grease. It is apparent that hoot sound of a very high level may be generated at a relatively high temperature, particularly when the properties at a low temperature of the base oil are not satisfactory.

In order to avoid the above-mentioned problem, a various kinds of esters, poly-alpha-olefin oils, and alkyldiphenylether oils, which have relatively high properties at a low temperature, have been used singly or in combination. It is noted, however, that generation of hoot sound at ultra low temperatures below −30 degree-C. could not be completely prevented, even when the above-mentioned substances are used. An effort has been continued in order to maintain the viscosity of a base oil at a lower value. Unfortunately, such an effort significantly reduces the service life at higher temperatures.

As will be appreciated from the foregoing, improvement in the properties at a low temperature and increase in the service life at a high temperature are contradictive with each other, so that it is difficult for them to consistent with each other. On the contrary, silicone oils have an extended service life and a superior lubricity at higher temperatures, as mentioned above. Silicone oils also have satisfactory properties at a low temperature and do not present an extremely high viscosity at a low temperature. Thus, the above-mentioned problem may be solved by using silicone oils as a base oil.

It is noted, however, that an extended service life, a satisfactory lubricity at a high speed, and hoot sound prevention capability at a ultra low temperature of a grease could not be obtained at the same time, by simply using a base oil having a satisfactory performance over a temperature range from a low temperature to a high-temperature. Rather, combination of such a base oil having the above properties with a thickening agent is an important subject. For example, and when 1,2-hydroxystearic lithium, which has been widely used as a thickening agent in prior art, is employed as a thickening agent to produce a grease, the resultant grease is changed into a flowable form at higher temperatures, even when a silicone oil, such as alkyldiphenylether oil, is used as a base oil. Thus, such a grease tends to be flown out from the locations to be lubricated and has a less heat-resistance, whereby it is not capable of presenting an extended service life. On the other hand, and when a alkyldiphenylether oil having a lower viscosity is employed so as to form a grease, the phenomena such as oil separation would be facilitated, so that the resultant grease tends to be flown out from a bearing. When organic bentonite powder, which is known in the art to be a heat-resistive thickening agent, is combined with a silicone oil so as to form a grease, the resultant grease tends to be easily hardened at higher temperatures. Thus, it could not maintain a satisfactory lubricity, whereby an extended service life could not be expected.

The thickening agent according to the invention is a diurea compound produced by reacting two amines having different structures with a diisocyanate. A grease, having been produced using urea compounds, as a thickening agent, other than those of the invention, presents an extended service life at higher temperatures, but it could not provide a satisfactory lubrication result at higher rotational speeds.

The lubrication mechanism of a bearing at higher temperatures is not sufficiently known and theoretically solved. It is believe, however, that the property of the constituents constituting thickening agents plays an important role in order to exert the above-mentioned functions.

The greases are in a semi-solid state at a room temperature, since the thickening agents therein have a three-dimensional network structure in a base oil, so that they may support oils by reason of their capillary force.

Such a structure may vary in various forms in accordance with increase in temperature. The bonded state may also vary significantly. Such states may be observed by checking the transition temperature representing change in crystalline state, using a differential thermal analysis. The transition temperature greatly depends upon constituents constituting a thickening agent used, but varies in a delicate manner depending upon the kinds and concentration of the base oil present therewith.

The grease filled within a bearing may increase its temperature, since shearing action and metal-to-metal contact are repeatedly caused under a severe condition, such as a high load and a high-speed rotation. The grease filled within a bearing also repeatedly experiences cycles between a room temperature and ultra low temperatures, due to stoppage of the bearing and atmosphere at low temperature.

Urea greases other than those in accordance with the invention may change their structural surfaces in their entirety as the above-mentioned cycles are repeated, so that phenomena, such as dissociation and hardening of oil, may be caused. This may lead to the worst condition in which a bearing is not sufficiently lubricated.

The constituents of the thickening agents according to the invention are featured by the diurea compounds which are formed by combining two kinds of amines having different constructions at an appropriate ratio and reacting them with an isocyanate. The portion of the two kinds of amines constituted by the compound formed by the straight chain aliphatic amines and the isocyanate may be dissolved in a base oil and has a less heat-resistive property. Thus, the portion will be dissolved easily, or flown to the raceway surface of the bearing, when the temperature in the bearing is increased, so as to form a strong lubrication film in its surface. This provides a satisfactory lubricity within the bearing at a high-speed rotation.

It is noted, however, that the above-mentioned property does not simply provide a very satisfactory result in terms of lubricity, since it causes flowing-out of the grease from the bearing. In order to avoid this, alicyclic amines having an increased performance in terms of heat-resistance are combined. The thus combined alicyclic amines are reacted with an isocyanate to form a portion constituting a diurea compound. This portion prevents softening and flowing-out of the grease and provide an increased heat-resistive property, so as to supplement the disadvantages of the aliphatic amines, whereby a heat resistance of the grease may be maintained.

Based on the above-mentioned concept, the construction of the thickening agent portion, constituting the lubricating grease according to the invention, includes two kinds of amines respectively bonded with diisocyanates, and two different kinds of amines bonded with diisocyanates, so as to form the thickening agent portion.

In a preferred configuration, the method of compounding and producing the grease should be studied, so that the compounds bonded with the isocyanates may be present in the system as much as possible. As the result of such studies, the most appropriate compounding ratio, together with the method of producing the grease have been found, whereby superior lubricating grease compositions have been obtained which may realize a satisfactory lubricity and an extended service life.

In order to confirm the advantages of the invention, three kinds of greases (Embodiments 1 to 3), having different constituents and different compounding ratios within the scope of the invention, were produced. These greases were compared with commercial greases (Comparative Example 1 to 3) for a clutch of a fluid fan. The results are given in FIGS. 1 and 2. The greases according to embodiments 1 to 3 are produced in the following manner. A half amount of a base oil indicated in FIG. 1 and the full amount of isocyanate are put into a reactor and heated to the temperature of 50 to 60 degree-C. Then, two kinds of amines and the remaining half amount of the base oil are put into a separate vessel and dissolved and heated to the temperature of 70 to 80 degree-C., so as to form a solution. This solution is carefully poured into the reactor and vigorously agitated therein for facilitation of the reaction. Since this reaction is exothermic, the temperature of the reactant is increased. Agitation and circulation through piping are continued for about 1 hour, so as to cause sufficient reaction and even dispersion. The circulation through piping is intermittently continued and the temperature of the reactant is increased. The reactant is maintained at the temperature of 170 to 180 degree-C. for about 1 hour. Thereafter, the reactant is cooled. When the reactant is cooled to the room temperature, it is finished by means of a three-staged roll mill, whereby an intended grease is obtained.

The properties of the base oils in the embodiments are given below.
1. Dimethyl-silicone Oil (Embodiment 1):
   kinetic viscosity; 35 mm$^2$/s (at 40 degree-C.)
   flash point; 300 degree-C.
2. Dimethyl-silicone Oil (Embodiment 2):
   kinetic viscosity; 70 mm$^2$/s (at 40 degree-C.)
   flash point; 315 degree-C.
3. Methylphenylene-silicone Oil (Embodiment 3):
   kinetic viscosity; 70 mm$^2$/s (at 40 degree-C.)
   flash point; 330 degree-C.
   The test condition is as follows:
      (a) consistency: according to JIS-K-2220.5.3;
      (b) dropping point according to JIS-2220.5.4;
      (c) low temperature torque: according to JIS-K-2220.5.14;
(d-1) Hoot Sound Confirmation Test 1:
   0.85 to 0.95 gr. of the grease according to one of the embodiments or the grease of one of the comparative examples is filled in a bearing 6203. A contact seal of rubber is attached to each side surface of the bearing, so as to seal the grease. The bearing is mounted on a housing. The bearing mounted on the housing is put into a cryostat at −40 degree-C. and cooled sufficiently. The bearing mounted on the housing is mounted on a bearing-rotating device set at the room temperature (test temperature: approximately −30 degree-C.). The inner ring, under the thrust load of 1.96 N, is rotated at the speed of 2,000 rpm. Generation of hoot sound is checked by means of audition.
(d-2) Hoot Sound Confirmation Test 2:
   1.7 to 1.9 gr. of the grease according to one of the embodiments or the grease of one of the comparative examples is filled in a bearing 6204. A contact seal of rubber is attached to each side surface of the bearing, so as to seal the grease. The bearing is mounted on a fan. The bearing mounted on the fan is mounted on a bearing-rotating device set at the room temperature. The inner ring, under no thrust load, is rotated at the speed of 1,700 rpm. Generation of hoot sound is checked by means of audition.
(3) Grease Life Test:
   1.7 to 1.9 gr. of the grease according to one of the embodiments or the grease of one of the comparative examples is filled in a bearing 6204. A non-contact seal of steel is attached to each side surface of the bearing. The bearing is mounted on a bearing-rotating device. The temperature of the bearing is maintained at 150 degree-C. The inner ring, under the thrust load and radial load of 67 N, is rotated at the speed of 10,000 rpm. The grease life is determined by the period of time during which the temperature of the bearing reaches 165 degree-C., due to the fact that the rotational torque becomes excessively high by reason of the deterioration of the grease filled in the bearing.

As will be appreciated from the results shown in FIG. 1, the greases of embodiments 1 to 3 are stable in the range of a low temperature rotational torque from 3.0 to 4.8 N-cm and do not generate any hoot sound. The service life of the greases is more than 6,000 hours.

On the contrary, the comparative example 1 (the combination of teflon, as a thickening agent, and a fluoro-silicone oil having a high viscosity, as a base oil), and the comparative example 2 (the combination of an urea compound, as a thickening agent, and an alkyldiphenylether oil, as a base oil) generate hoot sound under the condition of hoot sound confirmation test 1. The comparative example 3 (the combination of Lithium soap, as a thickening agent, and a methylphenyl-silicone oil, as a base oil) does not generate any hoot sound under the condition of hoot sound confirmation test 1, but have a short service life of 1,964 hours.

What is claimed is:
1. A grease-sealed rolling bearing for a fan of forced cooling in an engine of an automobile which restricts or prevents generation of hoot sound and provides service life of said grease of greater than 6,000 hours, which bearing is filled with a grease comprising a base oil, which base oil is a silicone oil having a viscosity of 30 to 500 mm$^2$/s at 40° C. and a viscosity of 30,000 mm$^2$/s or less at −30° C., and a thickening agent having a diurea compound, wherein the ratio of said base oil and said thickening agent is 2 to 30 wt-%, with the diurea compound having a general formula of:

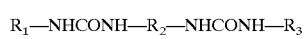

wherein
   $R_1$ is a straight chain saturated alkyl group having 6 to 18 carbon atoms,
   $R_2$ is a tolylene, diphenylmethylene or dimethylbiphenylene group, and R₃ is an alicyclic group,
wherein the ratio of the straight chain saturated alkyl group to the alicyclic group is within a range of 5 to 95 mol-% to 95 to 5 mol-%.

2. The bearing according to claim 1, wherein $R_1$ is a straight chain saturated alkyl group selected from the group consisting of n-propyl, isopropyl, n-butyl, isobutyl, s-butyl, n-pentyl, 3-methylbutyl, n-heptyl, n-octyl, 2-ethylhexyl, n-tetradecyl, n-hexadecyl, n-octadecyl and 3,5,5-trimethylhexyl, and $R_3$ is an alicyclic group selected from the group consisting of cyclopentyl, cyclohexyl and dihydroabietyl.

3. The bearing according to claim 2, wherein the silicone oil is dimethyl silicone,
$R_1$ is n-octadecyl,
$R_2$ is a diphenylmethylene group, and
$R_3$ is cyclohexyl,
wherein the ratio of the n-octadecyl group to the cyclohexyl group is within a range of 5 to 95 mol-% to 95 to 5 mol-%.

4. The bearing according to claim 2, wherein the silicone oil is methylphenyl silicone,
$R_1$ is n-octadecyl,
$R_2$ is a diphenylmethylene group, and
$R_3$ is cyclohexyl,
wherein the ratio of the n-octadecyl group to the cyclohexyl group is within a range of 5 to 95 mol-% to 95 to 5 mol-%.

5. A grease-sealed rolling bearing for a fan of forced cooling in an engine of an automobile which restricts or prevents generation of hoot sound and provides service life of said grease of greater than 6,000 hours, which bearing is filled with a grease consisting essentially of a base oil, which base oil is a silicone oil having a viscosity of 30 to 500 mm²/s at 40° C. and a viscosity of 30,000 mm²/s or less at −30° C., and a thickening agent having a diurea compound, wherein the ratio of said base oil and said thickening agent is 2 to 30 wt-%, with the diurea compound having a general formula of:

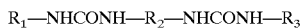

wherein
$R_1$ is a straight chain saturated alkyl group having 6 to 18 carbon atoms,
$R_2$ is a tolylene, diphenylmethylene or dimethylbiphenylene group, and
$R_3$ is an alicydlic group,
wherein the ratio of the straight chain saturated alkyl group to the alicyclic group is within a range of 5 to 95 mol-% to 95 to 5 mol-%.

6. The bearing according to claim 5, wherein $R_1$ is a straight chain saturated alkyl group selected from the group consisting of n-propyl, isopropyl, n-butyl, isobutyl, s-butyl, n-pentyl, 3-methylbutyl, n-heptyl, n-oclyl, 2-ethylhexyl, n-tetradecyl, n-hexadecyl, n-octadecyl and 3,5,5-trimethylhexyl, and $R_3$ is an alicyclic group selected from the group consisting of cyclopentyl, cyclohexyl and dihydroabietyl.

7. The bearing according to claim 6, wherein the silicone oil is dimethyl silicone, $R_1$ is n-octadecyl, $R_2$ is a diphenylmethylene group and $R_3$ is cyclohexyl.

8. The bearing according to claim 6, wherein the silicone oil is methylphenyl silicone, $R_1$ is n-octadecyl, $R_2$ is a diphenylmethylene group and $R_3$ is cyclohexyl.

* * * * *